(12) United States Patent
Xu et al.

(10) Patent No.: US 11,800,620 B2
(45) Date of Patent: Oct. 24, 2023

(54) LIGHT ENGINE CALIBRATION SYSTEMS AND METHODS

(71) Applicant: Alcon Inc., Fribourg (CH)

(72) Inventors: Jing Xu, Irvine, CA (US); Jason L. Lee, Anaheim, CA (US); Hari Krishna Kapparapu, Irvine, CA (US); Dean Richardson, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/807,770

(22) Filed: Jun. 20, 2022

(65) Prior Publication Data

US 2023/0027299 A1 Jan. 26, 2023

Related U.S. Application Data

(60) Provisional application No. 63/223,692, filed on Jul. 20, 2021.

(51) Int. Cl.
| | | |
|---|---|---|
| *H05B 47/105* | (2020.01) | |
| *A61B 90/30* | (2016.01) | |
| *H05B 45/20* | (2020.01) | |
| *H05B 45/10* | (2020.01) | |
| *A61B 17/00* | (2006.01) | |
| *A61F 9/007* | (2006.01) | |

(52) U.S. Cl.
CPC .......... *H05B 47/105* (2020.01); *A61B 90/30* (2016.02); *H05B 45/10* (2020.01); *H05B 45/20* (2020.01); *A61B 2017/00199* (2013.01); *A61B 2017/00725* (2013.01); *A61F 9/007* (2013.01)

(58) Field of Classification Search
CPC ...... H05B 47/105; H05B 45/10; H05B 45/20; H05B 47/17; A61B 90/30; A61B 2017/00199; A61B 2017/00725; A61F 9/007
See application file for complete search history.

(56) References Cited

U.S. PATENT DOCUMENTS

| | | |
|---|---|---|
| 8,371,695 B2 | 2/2013 | Papac et al. |
| 8,662,670 B2 | 3/2014 | Papac et al. |
| 8,688,401 B2 | 4/2014 | Papac et al. |
| 10,400,967 B2 | 9/2019 | Smith |
| 10,907,960 B1 * | 2/2021 | Bravo Orellana . G01B 11/2504 |
| 11,172,560 B2 | 11/2021 | Smith |

(Continued)

FOREIGN PATENT DOCUMENTS

| | | |
|---|---|---|
| EP | 2365773 B1 | 6/2019 |
| WO | 2006069002 A2 | 6/2006 |

OTHER PUBLICATIONS

Deurenberg, P., et al., "Achieving color point stability in RGB multi-chip LED modules using various color control loops," Proceedings of SPIE, IEEE, US, vol. 5941, Sep. 7, 2005, pp. 59410C-1, XP002428542, DOI: 10.1117/12.623020, ISBN: 978-1-62841-730-2.

*Primary Examiner* — Minh D A

(57) ABSTRACT

Embodiments of the present disclosure generally relate to systems and methods for calibrating light-emitting diode (LED) light engines. The systems and methods described herein include characterizing the performance of a red-green-blue (RGB) LED light engine so as to enable the display of calibrated, dimensionless output values that accurately reflect a perceived brightness of illumination generated by the light engine for a specific output color.

12 Claims, 15 Drawing Sheets

(56) References Cited

U.S. PATENT DOCUMENTS

| | | |
|---|---|---|
| 2015/0382425 A1 | 12/2015 | Lewis et al. |
| 2017/0006685 A1* | 1/2017 | Barron .................. H05B 45/20 |
| 2017/0172694 A1 | 6/2017 | Dos Santos |
| 2020/0154548 A1 | 5/2020 | Nagashima et al. |
| 2021/0018703 A1 | 1/2021 | Feingold et al. |

* cited by examiner

| SP1 No. | Sp2 x_soil | Sp3 y_soil | Sp4 Y_soil | Sp5 Red | Sp6 Green | Sp7 Blue | Sp8 Xa | Sp9 Ya | Sp10 Za | Sp11 xa | Sp12 ya | Sp13 Xb | Sp14 Yb | Sp15 Zb | Sp16 xb | Sp17 yb | Sp18 CWa[lm] | Sp19 CWb[lm] | Sp20 diffa_xy | Sp21 diffb_xy | Sp22 Matrix | Sp23 iter | Sp24 x_spec | Sp25 y_spec | Sp26 CW_spec | Sp27 diffs_xy |
|---|---|---|---|---|---|---|---|---|---|---|---|---|---|---|---|---|---|---|---|---|---|---|---|---|---|---|
| 1 | 0.3 | 0.3 | 50 | 4 | 32 | 57 | 1105.6 | 1087.9 | 1485.2 | 0.3005 | 0.2957 | 861.1 | 846.4 | 1481.4 | 0.27 | 0.2654 | 0.61 | 0.85 | 0.0043 | 0.0438 | 0 | 2 | 0.2827 | 0.2783 | 0.81 | 0.0278 |
| 2 | 0.4 | 0.4 | 50 | 79 | 19 | 46 | 1665.4 | 1178.1 | 1182.5 | 0.4137 | 0.2926 | 254.7 | 893.7 | 1185.1 | 0.3764 | 0.2881 | 0.95 | 0.91 | 0.0155 | 0.0397 | 0 | 2 | 0.3944 | 0.2776 | 0.86 | 0.0229 |
| 3 | 0.345 | 0.38 | 50 | 13 | 46 | 37 | 1227.2 | 1336.8 | 914.5 | 0.3528 | 0.3849 | 938.8 | 1015.5 | 1012.3 | 0.3165 | 0.3423 | 0.96 | 0.98 | 0.0089 | 0.0473 | 0 | 2 | 0.3329 | 0.3581 | 0.97 | 0.025 |
| 4 | 0.3 | 0.4 | 50 | 0 | 66 | 46 | 1314 | 1657.3 | 1161.5 | 0.3179 | 0.401 | 1015.8 | 1264.2 | 1285.1 | 0.2849 | 0.3546 | 1.16 | 1.21 | 0.018 | 0.0478 | 0 | 8 | 0.2989 | 0.3722 | 1.2 | 0.0278 |
| 5 | 0.4 | 0.3 | 50 | 40 | 45 | 28 | 1440.5 | 1418.6 | 649.7 | 0.4105 | 0.4049 | 1085.1 | 1066 | 771.2 | 0.3713 | 0.3648 | 1.04 | 1.02 | 0.0114 | 0.0454 | 0 | 2 | 0.3896 | 0.3793 | 1.02 | 0.0231 |
| 6 | 0.3 | 0.3 | 200 | 134 | 134 | 178 | 3664.1 | 3618.8 | 4932 | 0.3 | 0.2963 | 2821.3 | 2769.7 | 4427.1 | 0.2816 | 0.2765 | 2.68 | 2.77 | 0.0037 | 0.0299 | 0 | 1 | 0.2885 | 0.2834 | 2.63 | 0.0202 |
| 7 | 0.4 | 0.4 | 200 | 367 | 106 | 128 | 5331.9 | 4057.8 | 3622.6 | 0.4098 | 0.3118 | 4007.7 | 3051.1 | 3403.3 | 0.3831 | 0.2916 | 3.2 | 3.05 | 0.0153 | 0.0189 | 0 | 0 | 0.3867 | 0.2982 | 2.91 | 0.0038 |
| 8 | 0.345 | 0.38 | 200 | 156 | 163 | 111 | 3951.8 | 4341 | 3050.7 | 0.3464 | 0.3827 | 3013.7 | 3286.4 | 3138.5 | 0.3193 | 0.3482 | 3.12 | 3.16 | 0.0043 | 0.0409 | 0 | 1 | 0.3318 | 0.3609 | 3.11 | 0.0232 |
| 9 | 0.3 | 0.4 | 200 | 56 | 210 | 115 | 3216.3 | 4285.7 | 3145 | 0.3021 | 0.4025 | 2487.3 | 3260 | 3263.1 | 0.276 | 0.3618 | 2.97 | 3.1 | 0.0033 | 0.0451 | 0 | 0 | 0.2858 | 0.3767 | 3.07 | 0.0273 |
| 10 | 0.4 | 0.3 | 200 | 239 | 191 | 73 | 4604.7 | 4735.8 | 1988.3 | 0.4065 | 0.418 | 3461.9 | 3549 | 2287.2 | 0.3719 | 0.3813 | 3.44 | 3.37 | 0.0192 | 0.0337 | 0 | 0 | 0.3887 | 0.395 | 3.37 | 0.0124 |
| 11 | 0.3 | 0.3 | 450 | 348 | 316 | 366 | 7511.7 | 7464.2 | 9805.7 | 0.3031 | 0.3012 | 5727.8 | 5661.1 | 8140.1 | 0.2933 | 0.2899 | 5.52 | 5.61 | 0.0033 | 0.0121 | 0 | 0 | 0.2968 | 0.2932 | 5.37 | 0.0075 |
| 12 | 0.4 | 0.4 | 450 | 826 | 239 | 289 | 10822.9 | 8226.8 | 8316.4 | 0.4021 | 0.3028 | 8196.1 | 6161.8 | 6818.7 | 0.387 | 0.291 | 6.51 | 6.17 | 0.0035 | 0.0156 | 0 | 0 | 0.3951 | 0.2942 | 5.88 | 0.0076 |
| 13 | 0.345 | 0.38 | 450 | 377 | 433 | 217 | 8037.1 | 8866.8 | 5980 | 0.3497 | 0.3901 | 6098.8 | 6756.8 | 5826.4 | 0.3265 | 0.3617 | 6.42 | 6.45 | 0.0112 | 0.0261 | 0 | 0 | 0.3361 | 0.3718 | 6.39 | 0.0121 |
| 14 | 0.3 | 0.4 | 450 | 181 | 487 | 221 | 6560.4 | 8892.2 | 6050.4 | 0.3083 | 0.4116 | 5109.9 | 6729.4 | 5982.6 | 0.2867 | 0.3776 | 6.15 | 6.35 | 0.0143 | 0.026 | 0 | 0 | 0.2946 | 0.39 | 6.34 | 0.0114 |
| 15 | 0.4 | 0.3 | 450 | 539 | 429 | 163 | 8235.1 | 9494 | 4599 | 0.396 | 0.4067 | 6953.5 | 7107.5 | 4835.8 | 0.368 | 0.3761 | 6.9 | 6.76 | 0.0078 | 0.0399 | 0 | 0 | 0.3815 | 0.3877 | 6.74 | 0.0222 |
| 16 | 0.3 | 0.3 | 550 | 356 | 312 | 397 | 7668.9 | 7496.4 | 10622.1 | 0.2974 | 0.2907 | 5844.2 | 5688.3 | 8649.2 | 0.2896 | 0.2819 | 5.57 | 5.67 | 0.0097 | 0.0209 | 0 | 0 | 0.2821 | 0.2845 | 5.4 | 0.0174 |
| 17 | 0.4 | 0.4 | 550 | 1000 | 208 | 303 | 12163.4 | 8426.5 | 8426.7 | 0.4192 | 0.2904 | 9102.2 | 6298.5 | 7033.2 | 0.4057 | 0.2806 | 6.83 | 6.37 | 0.0215 | 0.0201 | 1 | 0 | 0.4136 | 0.2828 | 6.03 | 0.0219 |
| 18 | 0.345 | 0.38 | 550 | 446 | 524 | 242 | 9308.2 | 10500.1 | 6660.1 | 0.3517 | 0.3957 | 7055.1 | 7907.6 | 6465.2 | 0.3291 | 0.3688 | 7.5 | 7.52 | 0.018 | 0.0186 | 1 | 0 | 0.3386 | 0.3791 | 7.48 | 0.0065 |
| 19 | 0.3 | 0.4 | 550 | 197 | 564 | 279 | 7491.2 | 10044 | 7538.4 | 0.2983 | 0.4006 | 5745.7 | 7602.1 | 7145.5 | 0.2804 | 0.371 | 6.94 | 7.19 | 0.0014 | 0.0351 | 1 | 0 | 0.2869 | 0.362 | 7.17 | 0.0223 |
| 20 | 0.4 | 0.3 | 550 | 674 | 530 | 192 | 11178.8 | 11427.2 | 5149 | 0.4026 | 0.4117 | 8405.3 | 8557.1 | 5433.9 | 0.3753 | 0.3821 | 8.32 | 8.13 | 0.012 | 0.0305 | 1 | 0 | 0.3886 | 0.3936 | 8.11 | 0.0131 |
| 21 | 0.3 | 0.3 | 1200 | 777 | 681 | 866 | 15229.5 | 14863.1 | 21344.1 | 0.2962 | 0.2889 | 11188.9 | 15509.6 | 15653.2 | 0.2995 | 0.292 | 11.05 | 11.08 | 0.0117 | 0.008 | 1 | 0 | 0.2978 | 0.2892 | 10.68 | 0.011 |
| 22 | 0.4 | 0.4 | 1200 | 2181 | 454 | 661 | 23238.5 | 16078.7 | 17092.6 | 0.412 | 0.285 | 17416.1 | 12023.1 | 12853.3 | 0.4118 | 0.2843 | 13.04 | 12.13 | 0.0192 | 0.0197 | 1 | 2 | 0.413 | 0.2829 | 11.51 | 0.0215 |
| 23 | 0.345 | 0.38 | 1200 | 973 | 1143 | 528 | 18528.7 | 20707.7 | 13840.1 | 0.3491 | 0.3901 | 14001.9 | 15568.4 | 2231.3 | 0.335 | 0.3724 | 14.52 | 14.8 | 0.0109 | 0.0126 | 1 | 0 | 0.3406 | 0.379 | 14.79 | 0.0043 |
| 24 | 0.3 | 0.4 | 1200 | 417 | 1326 | 551 | 14817.4 | 20526.7 | 14259.6 | 0.2967 | 0.4114 | 11306.5 | 15509.6 | 12759.6 | 0.2857 | 0.3919 | 14.1 | 14.55 | 0.0139 | 0.0164 | 1 | 0 | 0.29 | 0.3999 | 14.66 | 0.01 |
| 25 | 0.4 | 0.3 | 1200 | 1470 | 1155 | 397 | 21976.9 | 22996.8 | 10094 | 0.3991 | 0.4067 | 16333.7 | 16789.7 | 10342.7 | 0.3786 | 0.3845 | 16.32 | 15.93 | 0.0068 | 0.0264 | 1 | 0 | 0.3883 | 0.3936 | 15.95 | 0.0133 |
| 26 | 0.3 | 0.3 | 2500 | 1620 | 1419 | 1804 | 28036.5 | 27180.8 | 39106.8 | 0.2972 | 0.2882 | 20804.2 | 20410.4 | 25950 | 0.3108 | 0.3034 | 20.23 | 20.09 | 0.0122 | 0.0113 | 1 | 0 | 0.3053 | 0.2954 | 19.55 | 0.097 |
| 27 | 0.4 | 0.4 | 2500 | 3200 | 960 | 1103 | 31540.4 | 24783.1 | 26639.2 | 0.3802 | 0.2997 | 23744.2 | 18637.4 | 15653.2 | 0.3866 | 0.3036 | 19.39 | 18.5 | 0.0199 | 0.0136 | 1 | 2 | 0.3842 | 0.3004 | 17.8 | 0.0158 |
| 28 | 0.345 | 0.38 | 2500 | 2026 | 2382 | 1100 | 33296.3 | 36393.4 | 26092.9 | 0.3476 | 0.38 | 25136.9 | 27422.9 | 20811.3 | 0.3426 | 0.3758 | 26.18 | 26.06 | 0.0026 | 0.0067 | 1 | 0 | 0.3445 | 0.3761 | 26.1 | 0.0039 |
| 29 | 0.3 | 0.4 | 2500 | 869 | 2762 | 1148 | 28428.4 | 35314.1 | 26714 | 0.2888 | 0.3992 | 20050.4 | 28703 | 21503 | 0.2938 | 0.3912 | 24.43 | 25.08 | 0.0015 | 0.0108 | 1 | 0 | 0.2952 | 0.394 | 25.38 | 0.0077 |
| 30 | 0.4 | 0.4 | 2500 | 3062 | 2407 | 827 | 37409.4 | 38341.8 | 20526.9 | 0.3886 | 0.3982 | 28328.4 | 28913.9 | 17870.6 | 0.3771 | 0.3849 | 27.92 | 27.43 | 0.0116 | 0.0274 | 1 | 0 | 0.3623 | 0.3913 | 27.48 | 0.0197 |

| | | a | |
|---|---|---|---|
| | | 1395.38 | 1051.03 |
| Flux % | Flux (lm) | corr Ya | corr Yb |
| 100% | 29.73 | 41485.4 | 31247.7 |
| 95% | 28.24 | 39411.2 | 29685.3 |
| 90% | 26.76 | 37336.9 | 28122.9 |
| 85% | 25.27 | 35262.6 | 26560.5 |
| 80% | 23.78 | 33188.3 | 24998.1 |
| 75% | 22.30 | 31114.1 | 23435.8 |
| 70% | 20.81 | 29039.8 | 21873.4 |
| 65% | 19.32 | 26965.5 | 20311.0 |
| 60% | 17.84 | 24891.3 | 18748.6 |
| 55% | 16.35 | 22817.0 | 17186.2 |
| 50% | 14.87 | 20742.7 | 15623.8 |
| 45% | 13.38 | 18668.4 | 14061.5 |
| 40% | 11.89 | 16594.2 | 12499.1 |
| 35% | 10.41 | 14519.9 | 10936.7 |
| 30% | 8.92 | 12445.6 | 9374.3 |
| 25% | 7.43 | 10371.4 | 7811.9 |
| 20% | 5.95 | 8297.1 | 6249.5 |
| 15% | 4.46 | 6222.8 | 4687.2 |
| 10% | 2.97 | 4148.5 | 3124.8 |
| 5% | 1.49 | 074.3 | 1562.4 |
| 0% | 0.00 | 0.0 | 0.0 |

| | | | Y intensity % | |
|---|---|---|---|---|
| a | 6.69402E-07 | 1.17344E-06 | | |
| b | 4.43115E-02 | 5.89776E-02 | | |
| | Y intensity | | Y intensity % | |
| | From corr Ya | From corr Yb | From corr Ya | From corr Yb |
| | 2990 | 2989 | 93.45% | 93.40% |
| | 2786 | 2785 | 87.07% | 87.03% |
| | 2588 | 2587 | 80.86% | 80.83% |
| | 2395 | 2394 | 74.84% | 74.82% |
| | 2208 | 2208 | 69.00% | 68.99% |
| | 2027 | 2027 | 63.34% | 63.33% |
| | 1851 | 1851 | 57.85% | 57.86% |
| | 1682 | 1682 | 52.55% | 52.56% |
| | 1518 | 1518 | 47.43% | 47.44% |
| | 1360 | 1360 | 42.49% | 42.51% |
| | 1207 | 1208 | 37.72% | 37.75% |
| | 1061 | 1061 | 33.14% | 33.17% |
| | 920 | 920 | 28.74% | 28.77% |
| | 785 | 785 | 24.52% | 24.54% |
| | 655 | 656 | 20.47% | 20.50% |
| | 532 | 532 | 16.61% | 16.64% |
| | 414 | 414 | 12.93% | 12.95% |
| | 302 | 302 | 9.43% | 9.44% |
| | 195 | 196 | 6.10% | 6.12% |
| | 95 | 95 | 2.96% | 2.97% |
| | 0 | 0 | 0.00% | 0.00% |

| a | | | |
|---|---|---|---|
| 1.07011 | 1.070707 | | |
| Y intensity % scale up | | Y intensity scale up | |
| From corr Ya | From corr Yb | From corr Ya | From corr Yb |
| 100.00% | 100.00% | 3200 | 3200 |
| 93.17% | 93.18% | 2981 | 2982 |
| 86.53% | 86.55% | 2769 | 2770 |
| 80.09% | 80.11% | 2563 | 2564 |
| 73.84% | 73.87% | 2363 | 2364 |
| 67.78% | 67.81% | 2169 | 2170 |
| 61.91% | 61.95% | 1981 | 1982 |
| 56.24% | 56.28% | 1800 | 1801 |
| 50.75% | 50.80% | 1624 | 1626 |
| 45.46% | 45.51% | 1455 | 1456 |
| 40.37% | 40.42% | 1292 | 1293 |
| 35.46% | 35.51% | 1135 | 1136 |
| 30.75% | 30.80% | 984 | 986 |
| 26.24% | 26.28% | 840 | 841 |
| 21.91% | 21.95% | 701 | 702 |
| 17.78% | 17.81% | 569 | 570 |
| 13.84% | 13.87% | 443 | 444 |
| 10.09% | 10.11% | 323 | 324 |
| 6.53% | 6.55% | 209 | 210 |
| 3.17% | 3.18% | 101 | 102 |
| 0.00% | 0.00% | 0 | 0 |

FIG. 7H

| | a | -1.61588E-06 | | a | 6.69402E-07 | 1.17344E-06 | | | | a | 1.07011 | 1.070707 | | |
|---|---|---|---|---|---|---|---|---|---|---|---|---|---|---|
| | b | 1.44616E-02 | 1395.38 | 1051.03 | b | 4.43115E-02 | 5.89776E-02 | | | | | | | |
| | | | | | Y intensity | | | Y intensity % | | | Y intensity % scale up | | Y intensity scale up | |
| Y intensity (max) | Flux % | Flux (lm) | corr Ya | corr Yb | | From corr Ya | From corr Yb | From corr Ya | From corr Yb | | From corr Ya | From corr Yb | From corr Ya | From corr Yb |
| 3200 | 100% | 29.73 | 41485.4 | 31247.7 | | 2990 | 2989 | 93.45% | 93.40% | | 100.00% | 100.00% | 3200 | 3200 |
| | 95% | 28.24 | 39411.2 | 29685.3 | | 2786 | 2785 | 87.07% | 87.03% | | 93.17% | 93.18% | 2981 | 2982 |
| | 90% | 26.76 | 37336.9 | 28122.9 | | 2588 | 2587 | 80.86% | 80.83% | | 86.53% | 86.55% | 2769 | 2770 |
| | 85% | 25.27 | 35262.6 | 26560.5 | | 2395 | 2394 | 74.84% | 74.82% | | 80.09% | 80.11% | 2563 | 2564 |
| | 80% | 23.78 | 33188.3 | 24998.1 | | 2208 | 2208 | 69.00% | 68.99% | | 73.84% | 73.87% | 2363 | 2364 |
| | 75% | 22.30 | 31114.1 | 23435.8 | | 2027 | 2027 | 63.34% | 63.33% | | 67.78% | 67.81% | 2169 | 2170 |
| | 70% | 20.81 | 29039.8 | 21873.4 | | 1851 | 1851 | 57.85% | 57.86% | | 61.91% | 61.95% | 1981 | 1982 |
| | 65% | 19.32 | 26965.5 | 20311.0 | | 1682 | 1682 | 52.55% | 52.56% | | 56.24% | 56.28% | 1800 | 1801 |
| | 60% | 17.84 | 24891.3 | 18748.6 | | 1518 | 1518 | 47.43% | 47.44% | | 50.75% | 50.80% | 1624 | 1626 |
| | 55% | 16.35 | 22817.0 | 17186.2 | | 1360 | 1360 | 42.49% | 42.51% | | 45.46% | 45.51% | 1455 | 1456 |
| | 50% | 14.87 | 20742.7 | 15623.8 | | 1207 | 1208 | 37.72% | 37.75% | | 40.37% | 40.42% | 1292 | 1293 |
| | 45% | 13.38 | 18668.4 | 14061.5 | | 1061 | 1061 | 33.14% | 33.17% | | 35.46% | 35.51% | 1135 | 1136 |
| | 40% | 11.89 | 16594.2 | 12499.1 | | 920 | 920 | 28.74% | 28.77% | | 30.75% | 30.80% | 984 | 986 |
| | 35% | 10.41 | 14519.9 | 10936.7 | | 785 | 785 | 24.52% | 24.54% | | 26.24% | 26.28% | 840 | 841 |
| | 30% | 8.92 | 12445.6 | 9374.3 | | 655 | 656 | 20.47% | 20.50% | | 21.91% | 21.95% | 701 | 702 |
| | 25% | 7.43 | 10371.4 | 7811.9 | | 532 | 532 | 16.61% | 16.64% | | 17.78% | 17.81% | 569 | 570 |
| | 20% | 5.95 | 8297.1 | 6249.5 | | 414 | 414 | 12.93% | 12.95% | | 13.84% | 13.87% | 443 | 444 |
| | 15% | 4.46 | 6222 | 4687.2 | | 302 | 302 | 9.43% | 9.44% | | 10.09% | 10.11% | 323 | 324 |
| | 10% | 2.97 | 4148.5 | 3124.8 | | 195 | 196 | 6.10% | 6.12% | | 6.53% | 6.55% | 209 | 210 |
| | 5% | 1.49 | 2074.3 | 1562.4 | | 95 | 95 | 2.96% | 2.97% | | 3.17% | 3.18% | 101 | 102 |
| | 0% | 0.00 | 0.0 | 0.0 | | 0 | 0 | 0.00% | 0.00% | | 0.00% | 0.00% | 0 | 0 |

FIG. 7I

LIGHT ENGINE CALIBRATION SYSTEMS AND METHODS

PRIORITY CLAIM

This application claims the benefit of priority of U.S. Provisional Patent Application Ser. No. 63/223,692 titled "LIGHT ENGINE CALIBRATION SYSTEMS AND METHODS," filed on Jul. 20, 2021, whose inventors are Jing Xu, Jason L. Lee, Hari Krishna Kapparapu and Dean Richardson, which is hereby incorporated by reference in its entirety as though fully and completely set forth herein.

FIELD

The present disclosure relates to systems and methods for calibrating light-emitting diode (LED) light engines, and more specifically, to systems and methods for calibrating red-green-blue (RGB) LED light engines to facilitate utilization of dimensionless output setting values reflecting an observed brightness of illumination.

BACKGROUND

Ophthalmic microsurgical procedures frequently require precision cutting and/or removing of various eye tissues. During such surgical procedures, proper illumination of the inside of the patient's eye is important, and an illumination probe of an ophthalmic illumination system is typically used to illuminate the surgical field. For example, a user, such as a surgeon or other medical professional, may insert the illumination probe into the patient's eye to illuminate the inside of the eye for a procedure. Typically, the probe is connected, through an optical fiber cable, to an optical port of the ophthalmic illumination system. The ophthalmic illumination system, which may be housed in a surgical console, includes a light engine (i.e., illumination source). The illumination system may also include other optical elements, such as collimating and condensing optics, that facilitate transmission of a light beam generated by the light engine into an optical fiber extending into the optical fiber cable and the probe.

The light engine is typically a red-green-blue (RGB) light-emitting diode (LED) light engine that can produce a range of different output colors and brightness levels that result from mixtures of light generated by the three LED colors when operated at various drive currents. However, because output of the individual LED colors is generally a nonlinear function of input current, the resultant combined output typically varies nonlinearly with input as well. As a result, adjustment by, e.g., the surgeon to a desired output brightness setting of the LED light engine does not result in a linear increase or decrease of observed illumination brightness, which may result in decreased efficiency of a surgical procedure and/or a frustrating user experience for the surgeon.

Accordingly, a need exists for LED illuminator calibration systems and methods that facilitate dimensionless output setting values that accurately reflect an observed brightness of the LED illuminator.

SUMMARY

The present disclosure relates to systems and methods for calibrating light-emitting diode (LED) light engines, and more specifically, to systems and methods for calibrating LED light engines to facilitate utilization of dimensionless output setting values reflecting a perceived brightness of illumination.

In certain embodiments, a method of producing calibrated illumination light with a light engine of an illumination system is provided, the method comprising: obtaining a first set of data for the light engine, wherein the first set of data includes measured output flux data of the light engine and color sensor luminance readings, wherein the measured output flux data and the color sensor luminance readings correspond to drive intensity data of a light engine input parameter; determining a first mapping between the measured output flux data and the drive intensity data; determining a second mapping between the measured output flux data and the color sensor luminance readings; determining a third mapping between the drive intensity data and the color sensor luminance readings, based on the first mapping and the second mapping; determining, based on the third mapping, a fourth mapping between a plurality of dimensionless output setting values of the illumination system and the drive intensity data; receiving one of the plurality of dimensionless output setting values from a user input; matching the one of the plurality of dimensionless output setting values to a corresponding drive intensity of the light engine input parameter using the fourth mapping; and producing, using the light engine, illumination light with a desired output flux.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 7A illustrates an example table of initial test data utilized during the method of FIG. 6, in accordance with certain embodiments of the present disclosure.

FIG. 7E illustrates an example experimental table as determined during the method of FIG. 6, in accordance with certain embodiments of the present disclosure.

FIG. 7G illustrates an example experimental table as determined during the method of FIG. 6, in accordance with certain embodiments of the present disclosure.

FIG. 7H illustrates an example experimental table as determined during the method of FIG. 6, in accordance with certain embodiments of the present disclosure.

FIG. 7I illustrates an example experimental table as determined during the method of FIG. 6, in accordance with certain embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
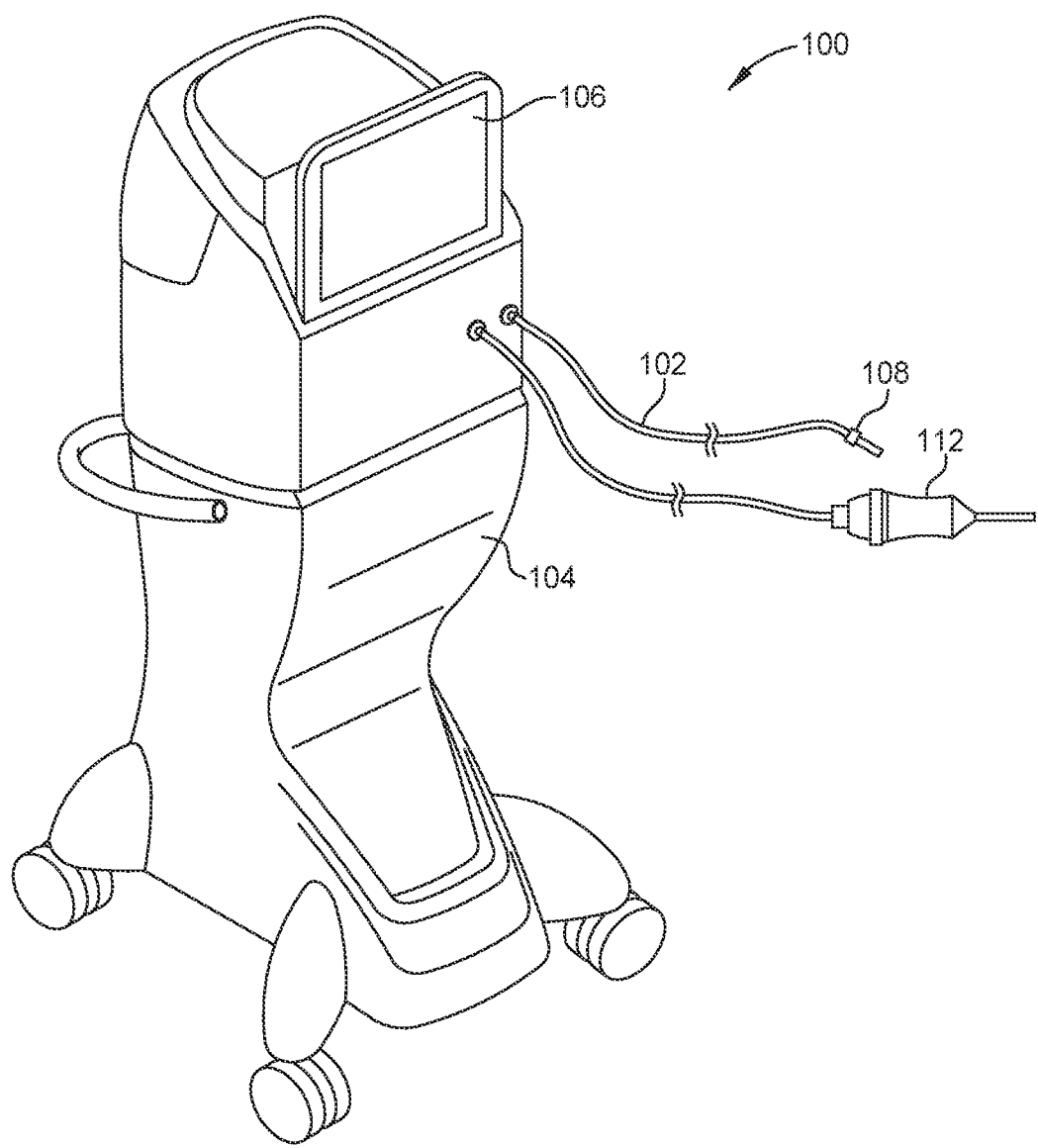
FIG. 1 illustrates an exemplary surgical console including an illumination system for ophthalmic surgical procedures, in accordance with certain embodiments of the present disclosure.

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's target tissue during use thereof. On the other hand, a proximal end, segment, or portion of the component refers to the end, segment, or portion that is distanced further away from the patient's target tissue.

As used herein, the term "about" may refer to a +/−10% variation from the nominal value. It is to be understood that such a variation can be included in any value provided herein.

The present disclosure relates to systems and methods for calibrating light-emitting diode (LED) light engines, and more specifically, to systems and methods for calibrating LED light engines such that a perceived brightness and color of a produced output light corresponds with a desired user input setting.

As described above, in certain existing LED illumination systems, the resultant output of the light engine is a nonlinear function of input, and so when adjusting the desired output settings of the light engine, the observed characteristics of the produced illumination light may not change in an intuitive, linear fashion. For example, an RGB LED illumination source can produce a range of different output colors and brightness levels that result from mixtures of light generated by the three LEDs when operated at various drive currents. Because the output of each individual LED is, in general, a nonlinear function of input current, the resultant combined output will also vary nonlinearly with input. Thus, when a user of an existing illumination system, e.g., a surgeon, attempts to increase or decrease a brightness of the illumination light during a surgical procedure by adjusting the settings of the light engine, the resulting delta in actual illumination light brightness may not correspond to the surgeon's desired setting adjustment. As a result, the surgeon may need to repeatedly adjust the settings of the light engine to obtain a desired brightness, thereby decreasing efficiency of the surgical procedure, as well as user experience for the surgeon.

Accordingly, the methods and systems described herein may be utilized to calibrate an illumination engine so that a change in observed brightness of a produced illumination light linearly corresponds to a user-input increase or decrease in brightness setting value. For example, certain embodiments described herein, a surgical system, e.g., surgical console, may include a display device displaying a desired illumination brightness setting value of an RGB LED illumination system as a percent of full scale, e.g., between 0-100%. A user may adjust the brightness setting percentage via a suitable toggle, such as a knob, button, or touch screen interface. Adjustments to the brightness setting percentage are communicated to a light engine interface, wherein a control module converts the brightness setting percentage to an appropriate electrical input resulting in an observed illumination brightness level corresponding to the adjusted brightness setting percentage.

FIG. 1 illustrates an example surgical system 100 that includes an illumination system, according to certain aspects of the present disclosure. In certain examples, surgical system 100 is a surgical system for ophthalmic surgery, including but not limited to surgical systems sold by Alcon of Fort Worth, Tex. The system 100 may be used in various ophthalmic procedures, such as an anterior segment procedure, a posterior segment procedure, a vitreoretinal procedure, a vitrectomy procedure, a cataract procedure, and/or other procedures. The surgical system 100 includes a console 104 and an associated display 106. The display 106 may display, for example, data relating to system operation and/or system performance during a surgical procedure, which may be arranged in a graphical user interface (GUI).

Generally, the console 104 includes one or more systems or subsystems that enable a surgeon to perform a variety of surgical procedures, such as ophthalmic surgical procedures. For example, the console 104 may include the illumination system (labeled 200 in FIG. 2) with a light source producing illumination light that can be directed into a body cavity to allow a surgeon to operate therein. Light generated by the light source may be transmitted into the eye via an optical fiber that is disposed within an optical fiber cable 102 and that distally terminates at illumination probe 108. In some implementations, the light may pass through one or more optical elements, such as, for example, one or more lenses, mirrors, and/or attenuators, before or after entering the optical fiber. In some implementations, an access instrument, generally referred to as a cannula (labeled 310 in FIG. 3) may be utilized to pass the optical fiber and/or the illumination probe 108 of the illumination system into the eye. The cannula may be used to make or to open an incision through the wall of a body cavity, e.g., through the sclera of an eye. In some instances, the cannula may be inserted into an incision made by a user, such as a surgeon or other medical professional, using another surgical tool. The cannula typically includes a lumen through which a surgeon may insert one or more surgical tools or probes in order to perform a surgical procedure within the cavity.

An exemplary surgical tool, which is illustrated as a handpiece 112, may be coupled to the console 104 and may form a part of the surgical system 100. The handpiece 112 represents any type of ophthalmic surgical probe, including, for example, a vitrectomy probe, an illumination probe, an aspiration probe, an irrigation probe, a phacoemulsification device, a diathermy probe, or other types of devices. In the illustrated implementation, the handpiece 112 is a vitrectomy probe used to remove vitreous from an eye. The handpiece 112 may be coupled to one or more systems or subsystems included in the console 104. For example, the handpiece 112 may be coupled to a vitrectomy system that controls a pump and/or a vacuum for use in the removal of vitreous. The vitrectomy system may also provide power to the handpiece 112 and control operation of the handpiece 112. In some implementations, the handpiece 112 may be a vitreous cutter, such as, for example, an oscillating vitreous cutter.

Figure 2:
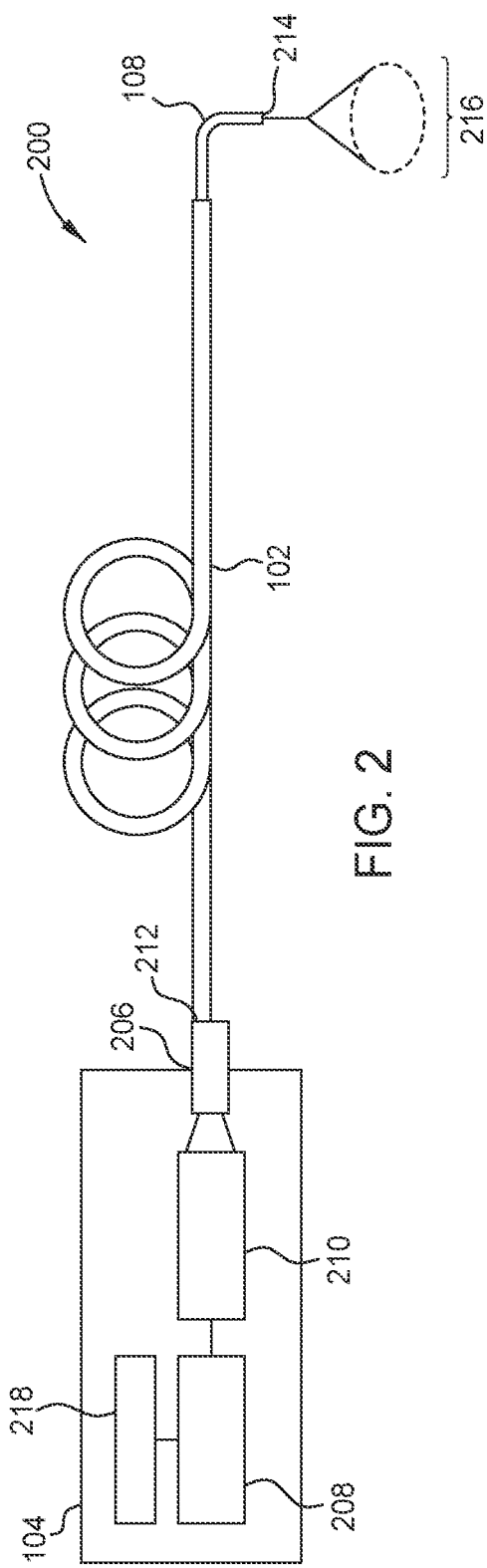
FIG. 2 illustrates the illumination system of FIG. 1, in accordance with certain embodiments of the present disclosure.

FIG. 2 illustrates the illumination system 200 of FIG. 1, according to certain aspects of the present disclosure. The illumination system 200 may include the illumination probe 108, e.g., an endoilluminator or chandelier endoilluminator, coupled to console 104 via the optical fiber cable 102, which includes one or more optical fibers disposed therein. A proximal end 212 of the optical fiber cable 102 is coupled to the console 104 using a connector 206.

The console 104 provides a light source, which in the example of FIG. 2, includes a light engine 208 and an optical condensing element 210. The light engine 208 is in communication with a controller 218, and may include any suitable type of light source, such as one or more light emitting diodes (LEDs). For example, in certain embodiments, light engine 208 includes one or more sets of red-green-blue (RGB) LEDs. In operation, upon receiving a control signal from the controller 218, the light engine 208 converts the control signal into an electrical input that is provided to one or more drive circuits and/or electrical components for driving the light source, e.g., RGB LEDs. In certain embodiments, the control signal and/or electrical input, includes one or more of, e.g., a pulse width modulation (PWM) duty cycle, drive current, or other suitable type of control parameter appropriate for the circuit design and driving scheme of the illumination system 200. After converting the control signal and providing the appropriate electrical input to the light source, the light engine 208 emits a light beam that is then condensed and focused by the optical condensing element 210 on an opening at the proximal end of connector 206, where the opening exposes the proximal ends of one or more optical fibers extending through the optical fiber cable 102. The illumination probe 108 is then operable to transmit the light beam received from the light source such that light is projected from a distal end 214 thereof to illuminate an area 216, such as a portion of the inner eye during ophthalmic surgery.

Figure 3:
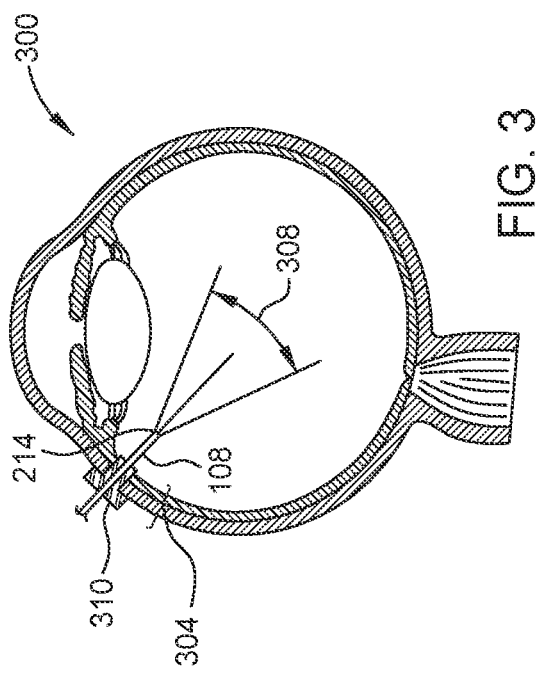
FIG. 3 illustrates a portion of an illumination probe of the illumination system of FIG. 1 during an ophthalmic surgical procedure, in accordance with certain embodiments of the present disclosure.

For example, FIG. 3 illustrates a cross-sectional view of an eye 300 having a portion of the illumination probe 108 disposed through the wall 304 thereof, via cannula 310, to provide a source of light in the internal portion of the eye globe. The distal end 214 of the illumination probe 108 illuminates an internal area of the eye 300 with a light beam 308.

Figure 4:
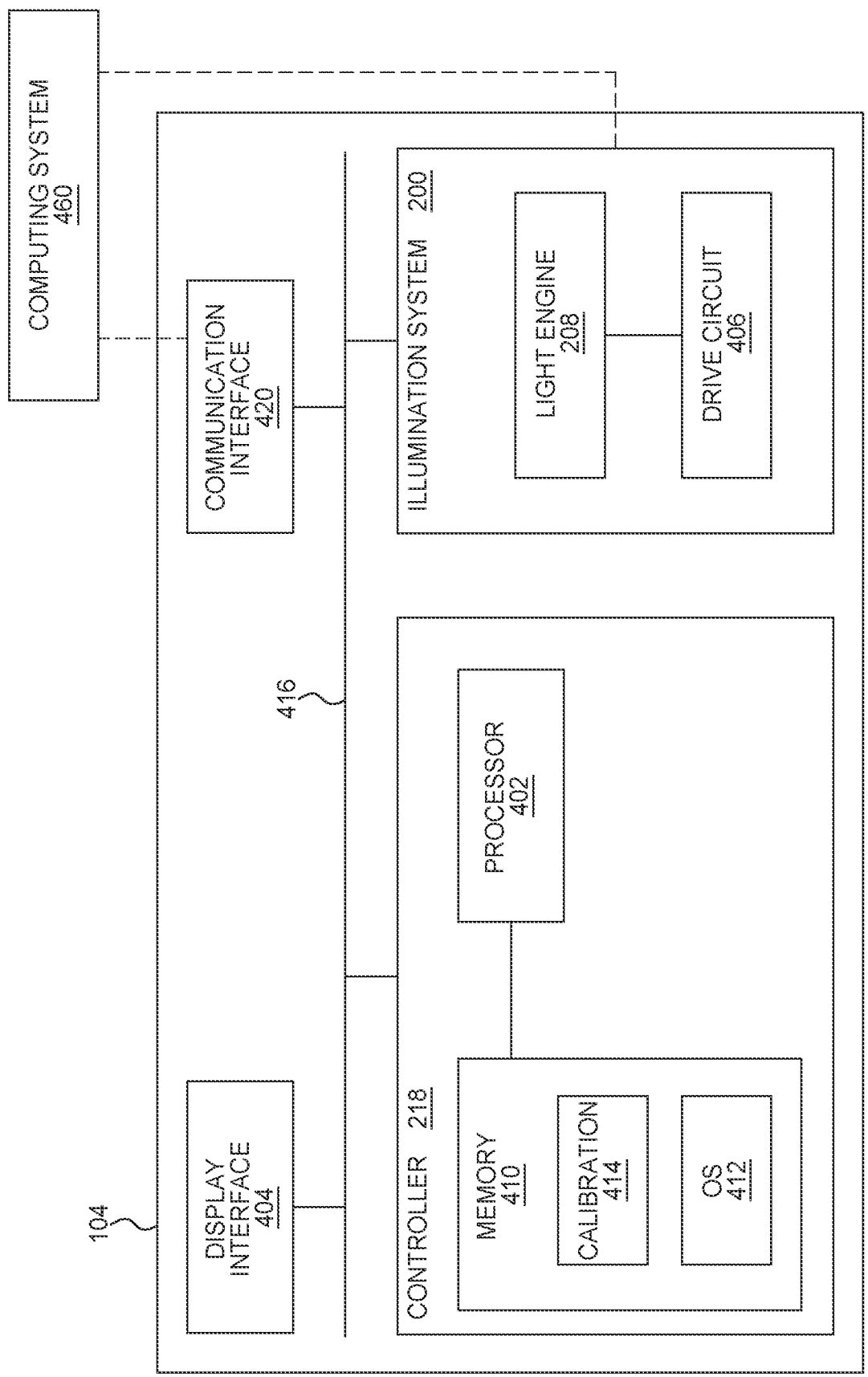
FIG. 4 illustrates a block diagram of selected components of a light engine controller of the illumination system of FIG. 1, in accordance with certain embodiments of the present disclosure.

FIG. 4 illustrates a block diagram of selected components of an implementation of a controller, such as controller 218, that is associated with or coupled to an illumination system, such as illumination system 200, that is part of a surgical console, such as console 104, as described above with reference to FIGS. 1-2.

As shown in FIG. 4, controller 218 includes processor 402 in communication with memory 410. Controller 218 is further communicatively coupled to display interface 404 and communication interface 420 of console 104, as well as illumination system 200, via bus 416. In certain embodiments, controller 218 is configured to interface with the illumination system 200 and other components of the console 104 through bus 416. In some implementations, communication interface 420 may be configured to enable controller 218 to connect, wired or wirelessly, to an external computing system, e.g., computing system 460, through a network. The network may include one or more switching devices, routers, local area networks (e.g., an Ethernet), wide area networks (e.g., the Internet), and/or the like. Computing system 460 may be an on-premise computing system or correspond to computing resources provided by a private or public cloud. Controller 218 may also be connected to one or more displays, such as display 106, via display interface 404.

Memory 410 may include persistent, volatile, fixed, removable, magnetic, and/or semiconductor media. The memory 410 may be configured to store one or more machine-readable commands, instructions, data, and/or the like. In some implementations, as shown in FIG. 4, memory 410 may include one or more sets and/or sequences of instructions, such as an operating system 412, a calibration application 414, and the like. Examples of operating system 412 may include, but are not limited to, UNIX or UNIX-like operating system, a Windows® family operating system, or another suitable operating system.

The calibration application 414 may be configured to perform light engine calibration operations as described herein including, but not limited to, operations related to calibrating an observed output flux or brightness relative to a received setting value, and the like. For example, light engine calibration application 414 may configure controller 218 to perform a set of operations, such as operations 600, to determine one or more functions for converting a desired illumination setting (e.g., desired brightness, etc.), provided by a user, into a calibrated control signal for light engine 208. Once determined, the functions may then be stored in memory 410 for retrieval during operation of illumination system 200. For example, during operation of the illumination system 200, a user may input a desired illumination setting through a user interface of display 106. Processor 402 then uses the desired illumination setting as input into the one or more determined functions and outputs a calibrated control signal that is then transmitted to illumination system 200. Drive circuit 406 of the light engine 208 then converts the calibrated control signal into a corresponding electrical input that is provided to the light engine 208 to produce an illumination light corresponding to the desired illumination setting.

Note that although processor 402 and memory 410 are shown as components of controller 218, illumination system 200 may comprise its own dedicated processor and memory, which may perform the same or similar functions as processor 402 and memory 410 described above. That is, illumination system 200 may include a dedicated processor and memory, and the dedicated memory may include a calibration application configured to perform light engine calibration operations as described herein. In such embodiments, upon determining one or more light engine calibration functions, the functions may then be stored in memory 410 of controller 218 for use during operation of illumination system 200.

In certain embodiments, light engine calibration operations are performed on a separate computing system, e.g., computing system 460, in communication with the console 104 and/or illumination system 200. In such embodiments, computing system 460 comprises a dedicated processor and memory that stores the calibration application for performing the light engine calibration operations (e.g., operations 600) described herein for deriving the one or more functions for converting a desired illumination setting into a calibrated control signal for light engine 208. In certain embodiments, the one or more functions may then be sent and stored in memory 410 or a memory that is dedicated to illumination system 200.

Figure 5:
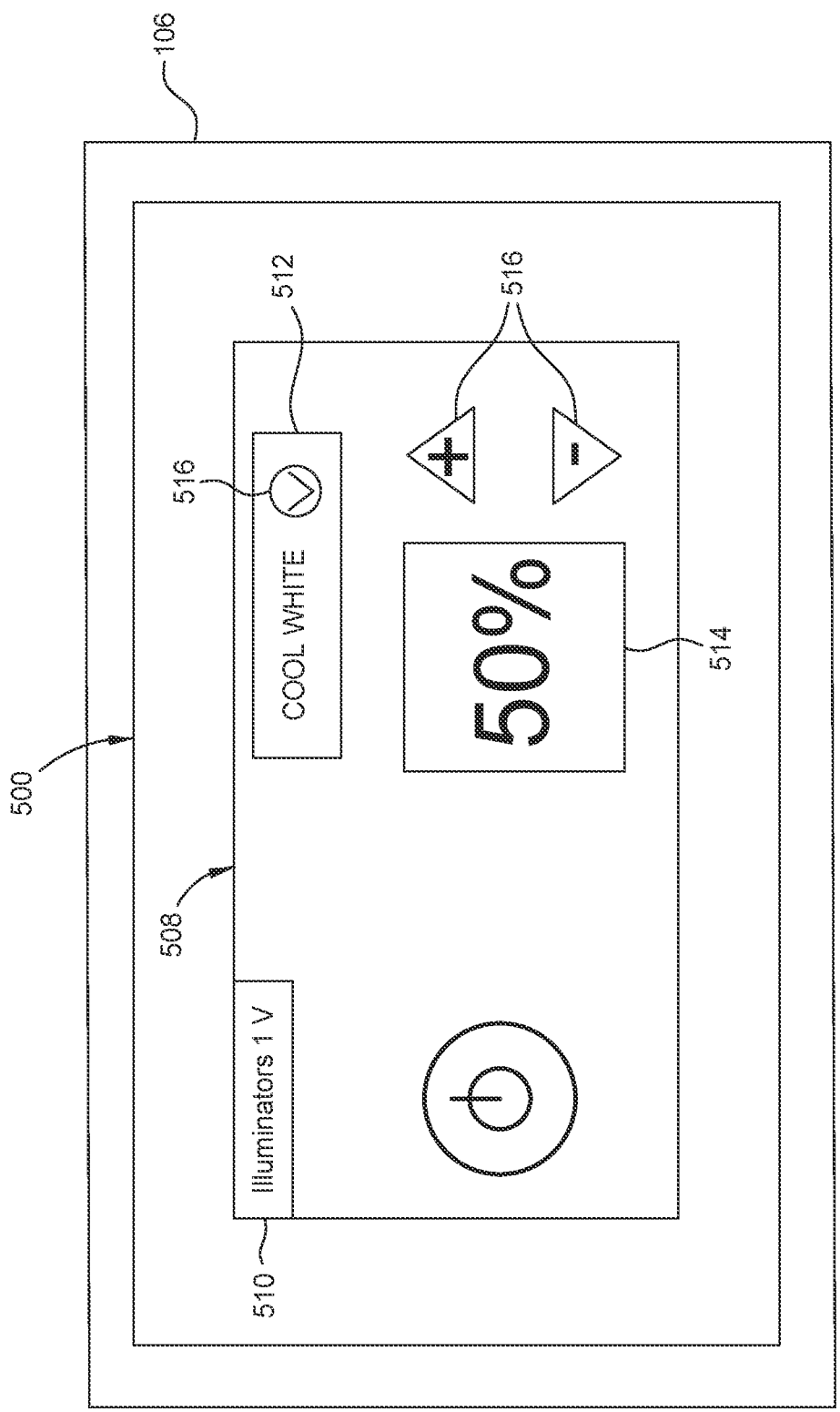
FIG. 5 illustrates an example graphical user interface of the surgical system of FIG. 1, in accordance with certain embodiments of the present disclosure.

FIG. 5 illustrates an example GUI 500 that may be displayed on, e.g., display 106 of the surgical system 100. The GUI 500 may display, for example, data relating to system operation and/or system performance during a surgical procedure, and/or data relating to operation or performance of one of more surgical devices, e.g., handpiece 112. The GUI 500 may further display one or more graphical control elements such as windows, toolbars, menus, buttons, icons, and the like, which allow a user, e.g., surgeon, to adjust one or more modes, parameters, or settings during the surgical procedure, as well as alternate between displayed data.

In the example shown in FIG. 5, the GUI 500 includes a window 508 for displaying information related to the operations of one or more illuminators (e.g., illumination probe 108) of the illumination system 200. The displayed information may include illumination output parameters or settings of the one or more illuminators, such as color and flux (e.g., brightness). For example, as shown in FIG. 5, a single illuminator (e.g., depicted as "Illuminator 1") is identified and displayed with output settings thereof. The displayed output settings include a color setting 512, which is currently set to "Cool White," that identifies the current color of the illumination light emitted by Illuminator 1, as well as a flux or brightness setting 514 that identifies the current flux thereof as a unitless value on a percentage scale of 0-100%. Accordingly, the displayed flux setting 514 corresponds to a proportion of the maximum producible flux for the illumination light by a corresponding light engine of Illuminator 1.

In certain embodiments, values of, e.g., the color setting 512 and the brightness setting 514, may be adjusted by the surgeon via one or more toggles 516 or other suitable control element of the window 508. For example, during a surgical procedure, the surgeon may control performance of one or more illuminators of the illumination system 200 via the GUI 500, e.g., by pressing one or more toggles 516 to change the value(s) of a displayed illumination output setting. Changing the value of a displayed output setting, in turn, may send a signal to the controller 218 to adjust the performance of a corresponding light engine 208 of the illuminator by, e.g., modulating an electrical input parameter applied thereto. However, as described above, when the light engine 208 is an RGB LED light engine, the resultant output of the light engine 208 is a nonlinear function of input. Thus, in certain existing systems, when adjusting a brightness setting of the light engine 208, e.g., a flux setting 514, the resulting illumination light brightness may not correspond to the brightness setting adjustment in an intuitive, linear fashion. As a result, a surgeon may need to repeatedly adjust the flux setting 514 of the light engine 208 to obtain a desired brightness, thereby decreasing efficiency of the surgical procedure, as well as the user experience for the surgeon. The proceeding description addresses this deficiency by providing methods of calibrating an RGB LED light engine so that an observed brightness of a produced illumination light linearly corresponds to a user-input increase or decrease in an output setting value. In certain embodiments, the methods described below may be performed by a computer or controller of the surgical system 100 or illumination system 200, e.g., the controller 218. For example, the methods described below may be performed by a computer (e.g., a personal computer in a laboratory setting or a cloud-based computing resource (e.g., NumPy notebook)) running a spreadsheet or tabular data software.

Figure 6:
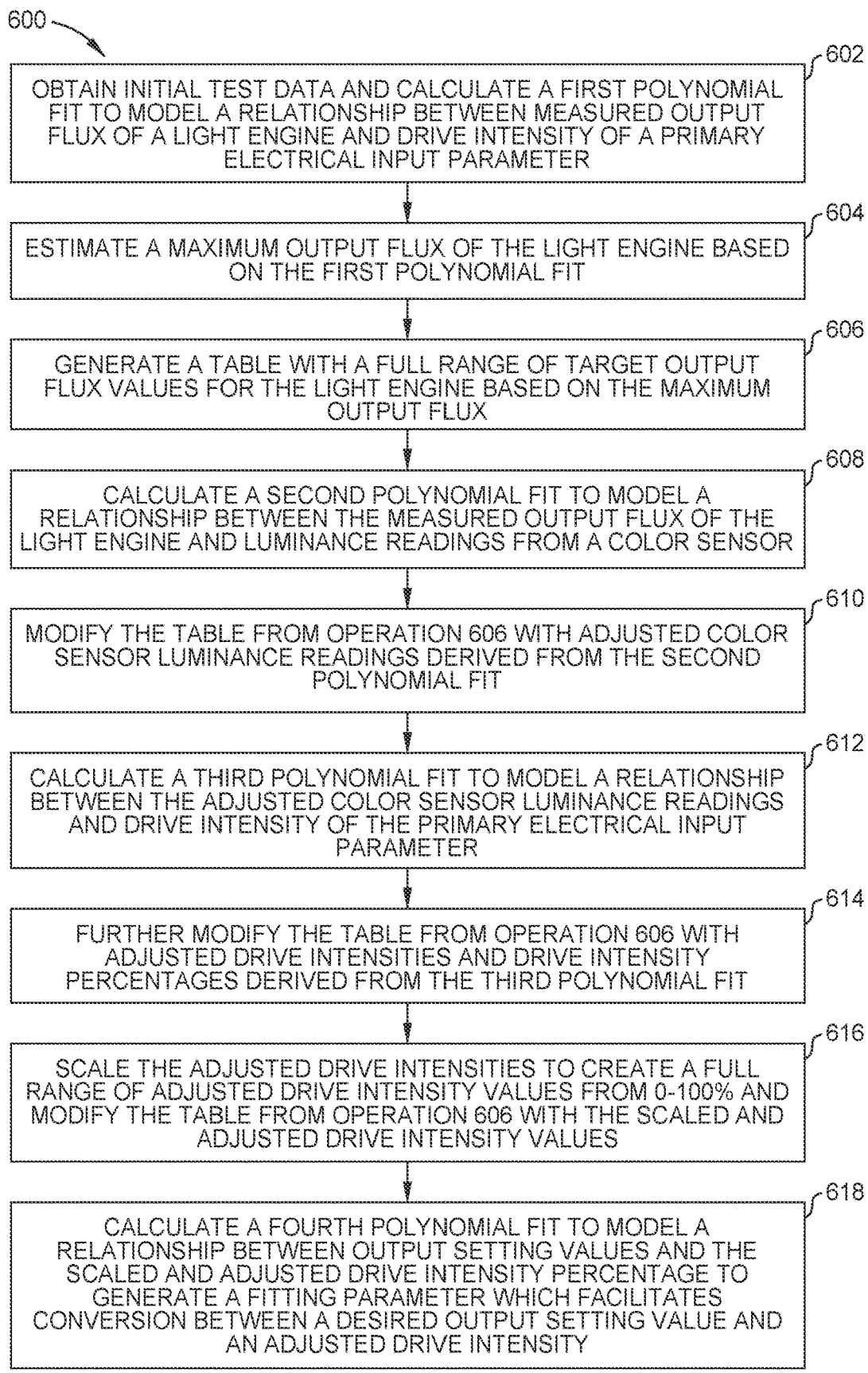
FIG. 6 illustrates flow diagram of a method for calibrating a light engine of the illumination system of FIG. 1, in accordance with certain embodiments of the present disclosure.

FIG. 6 illustrates a flow diagram of a method 600 for calibrating an RGB LED light engine, e.g., light engine 208, of an illumination system, according to certain aspects of the present disclosure. FIGS. 7A-7J schematically illustrate operations of the method 600, according to certain aspects of the present disclosure. Accordingly, FIG. 6 and FIGS. 7A-7J are herein described together for clarity.

Calibration of the RGB LED light engine 208 involves analysis of input-output data exhibited by light engine 208 and a sequence of empirical fits and scaling normalizations thereof. The sequence of empirical fits and scaling normalizations yields a set of constants that enable a unitless output setting value (e.g., ranging between 0-100%) to be mapped accurately to corresponding RGB LED drive parameters for desired colors. As a result, a consistent and intuitive relationship is established between a user's output setting value adjustments and the perceived changes in illumination light brightness, which are customized to the individual light engine 208. Thus, the calibration of the RGB LED light engine 208 enables reliable and repeatable conversion of desired output setting values, which are selected by the user, to RGB LED drive parameters which produce corresponding observed (e.g., output) illumination brightness levels, while maintaining a desired color balance, in real time.

Turning now to FIG. 6, at operation 602 of method 600, initial test data for the light engine 208 is obtained, and a first polynomial fit or function is calculated therewith to model a relationship between output flux of the light engine 208 and a drive intensity of a primary electrical input parameter of light engine 208 for a specific pre-set color. Test data for the light engine 208 may include any suitable set of test or inspection data that provides exhibited output characteristics, such as colorimetric characteristics, of the light engine 208 for one or more pre-set colors across a range of one or more electrical input parameters. In certain embodiments, electrical input parameters include drive current, duty cycles of pulse-width modulation (PWM) signals, and the like.

For example, in certain embodiments, test data for the light engine 208 is collected by applying an LED drive current to the light engine 208, adjusting a length of time of a duty cycle of a PWM signal thereof, and measuring output characteristics, e.g., output flux, of the light engine 208 across the range of duty cycle times via one or more sensors. In such embodiments, adjusting the duty cycle of the PWM signal rather than adjusting the applied drive current, e.g., via continuous knob adjustment, enables maintenance of a fixed current value during testing, thereby providing predictability and localization to a single input point on the calculated input-output curve and avoiding certain issues relating to non-linearity of input to observed output of LED light engines, e.g., light engine 208. In certain embodiments wherein duty cycle times of PWM signals are utilized as the electrical input parameter, the PWM signals are filtered and converted to analog drive current prior to application to the light engine 208. In certain embodiments, output characteristics are collected across a range of duty cycle times for each of a plurality of different drive inputs, e.g., drive currents.

An exemplary table 700 with obtained test data specific for the particular light engine 208 is illustrated in FIG. 7A. As shown, table 700 includes, at the least, data relating to chromaticity and luminance of the light engine 208 for a plurality of pre-set colors, which are organized according to the Commission Internationale de l'Eclairage (CIE) xy color space. For example, the CIE system characterizes colors by two color coordinates x and y, shown in columns Sp2 and Sp3 of table 700, respectively, as well as a luminance parameter Y, shown in column Sp4. Note that, in some examples, the numbers in the Sp4 column are not exactly CIE Y, but highly non-linearly correlated therewith. Thus, in table 700, each different pair of coordinates in columns Sp2 and Sp3 (across a row) corresponds to a particular pre-set color, and the luminance parameter Y in column Sp4 corresponds to a drive value of an electrical input parameter applied to light engine 208 for propagating light with the pre-set color. For purposes of illustration, five example pairs of x, y color coordinates (0.3, 0.3; 0.4, 0.3; 0.345, 0.38; 0.3, 0.4; and 0.4, 0.4) are shown in table 700, each representing a different pre-set color desired by a user. In order to calibrate the light engine 208 for each of the five pre-set color coordinates, test data for the light engine 208 is collected for each pre-set color, and the remaining operations of method 600 are performed individually therewith, either simultaneously or sequentially. Accordingly, each row (e.g., line) of test data in table 700 is specific to the corresponding pre-set color coordinates in columns Sp2 and Sp3.

In certain embodiments, the test data is collected and provided by a manufacturer of the light engine 208. In certain embodiments, the test data is collected by a manufacturer or assembler of a surgical system or illumination system, e.g., systems 100 or 200, respectively. Typically, the test data, e.g., including measured raw output characteristics of the light engine 208 across a range of drive values for the primary electrical input parameter, is collected using one or more color sensors, which may be internal to the light engine 208 or illumination system 200. In the example of FIG. 7A, data from two color sensors is shown, though only one sensor is sufficient for the methods herein. Because each light engine has a unique set of test data, in certain embodiments, test data is collected for each light engine (e.g., light engine 208) that is to be used in a surgical system (e.g., surgical system 100), and the method 600 is performed separately therewith.

Figure 7B:
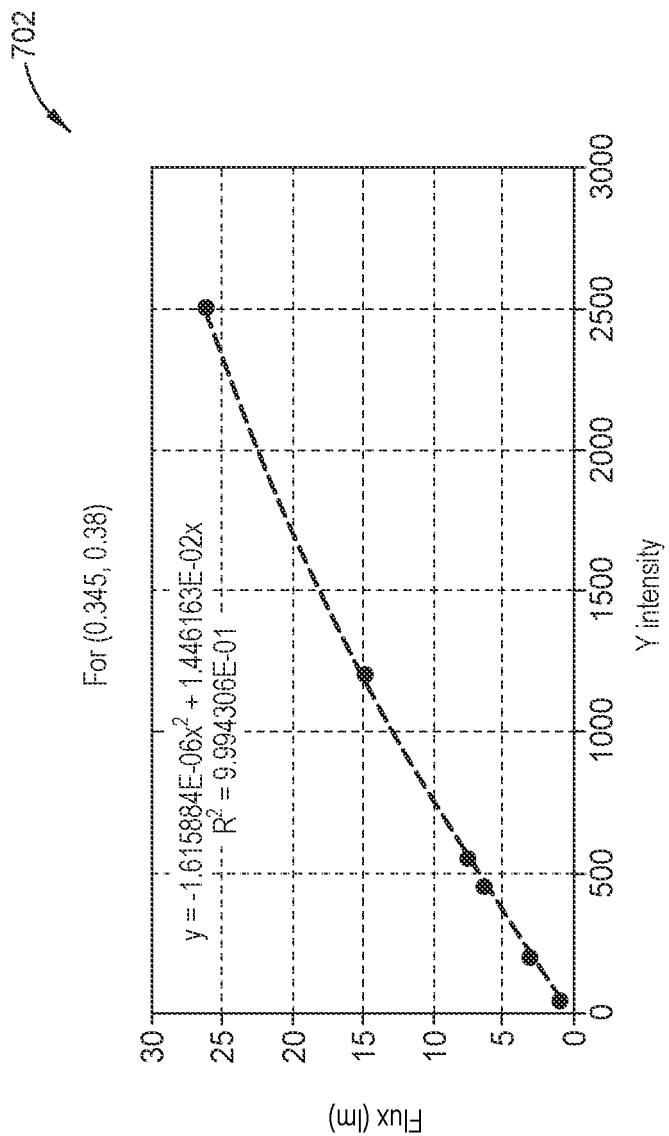
FIG. 7B illustrates an example fitted polynomial curve as determined during the method of FIG. 6, in accordance with certain embodiments of the present disclosure.

As shown in FIG. 7A, the table 700 includes measured output flux values of light engine 208 in column Sp26, as measured by a calibrated radiometric instrument in lumens, and a range of corresponding drive intensity values for a particular electrical input parameter in column Sp4. In the current example, PWM duty cycles are utilized as the electrical input parameter. As described above, at operation 602, the relationship between the drive intensity values in Sp4 and the measured output flux values in Sp26 is determined and analyzed for a specific color, and a fitted polynomial curve (also referred to herein as a first function), is generated therefor. An example fitted curve of the relationship for color coordinates (0.345, 0.38), wherein the drive intensity is plotted along the X-axis and the measured output flux is plotted along the Y-axis, is illustrated in graph 702 of FIG. 7B. As shown, the example fitted curve is characterized by the following polynomial function:

$$\text{Flux (lm)} = (-1.615884e^{-06}) \times (\text{drive value})^2 + (1.446163e^{-02}) \times (\text{drive value}).$$

At operation 604, upon forming a fitted polynomial curve to model the relationship between the measured output flux of the light engine 208 in lumens and the drive intensity of the primary electrical input parameter, the polynomial fit is used to estimate an output flux of the light engine 208 at a maximum drive intensity value, i.e., the estimated maximum output flux. Generally, the maximum drive intensity value is the maximum input parameter value achievable by the illumination system 200 in which the light engine 208 is to be installed (e.g., assembled with). For example, in embodiments where PWM signals are utilized as the input parameter, the maximum drive intensity value is the maximum PWM duty cycle allowed by the illumination system 200. In such embodiments, the maximum duty cycle may be limited by, e.g., a communication rate between a controller of the surgical system 100 or illumination system 102, e.g., light engine controller 218, and the light engine 208 or a clock rate of the control signal. Accordingly, the estimated maximum output flux, for purposes of the present disclosure, corresponds to a 100% output setting value for the light engine 208 when converted to unitless output setting values. Thus, if a user, e.g., a surgeon, were to select a desired output flux setting value of 100%, the light engine 208 would produce an observed output substantially equal to the estimated output flux determined at operation 604.

For illustrative purposes, an example calculation of the estimated maximum output flux is shown below. The below calculation utilizes the polynomial fit, or first function, derived in FIG. 7B for color coordinates (0.345, 0.38), and further utilizes an example maximum drive intensity value of 3200, which corresponds to a maximum PWM duty cycle of a system. Note that for any given surgical and/or illumination system, the maximum drive intensity value of an electrical input parameter may be different, and may depend on the processing and/or computing specifications thereof.

$$29.73 \text{ (lm)} = (-1.615884e^{-06}) \times (3200)^2 + (1.446163e^{-02}) \times (3200).$$

Utilizing the polynomial fit above, the calculated maximum output flux of 3200 is 29.73 lumens, and so 29.73 lumens in this example may therefore correspond to 100% flux for the specific color coordinates (0.345, 0.38).

At operation 606, now having the estimated maximum output flux of the light engine 208 for color coordinates (0.345, 0.38), a mapping of a full range of target outputs, e.g., in lumens, for each desired output setting value step, e.g., in percentages, is determined. In other words, a plurality of target output flux values for the light engine 208 are mapped to unitless output setting values on a percentage scale of 0-100%. The target output flux values for each output setting value may be calculated utilizing the following formula:

$$\text{Flux(lm)} = (\text{estimated maximum output flux}) \times (\text{desired output setting value(\%)})$$

Figure 7C:
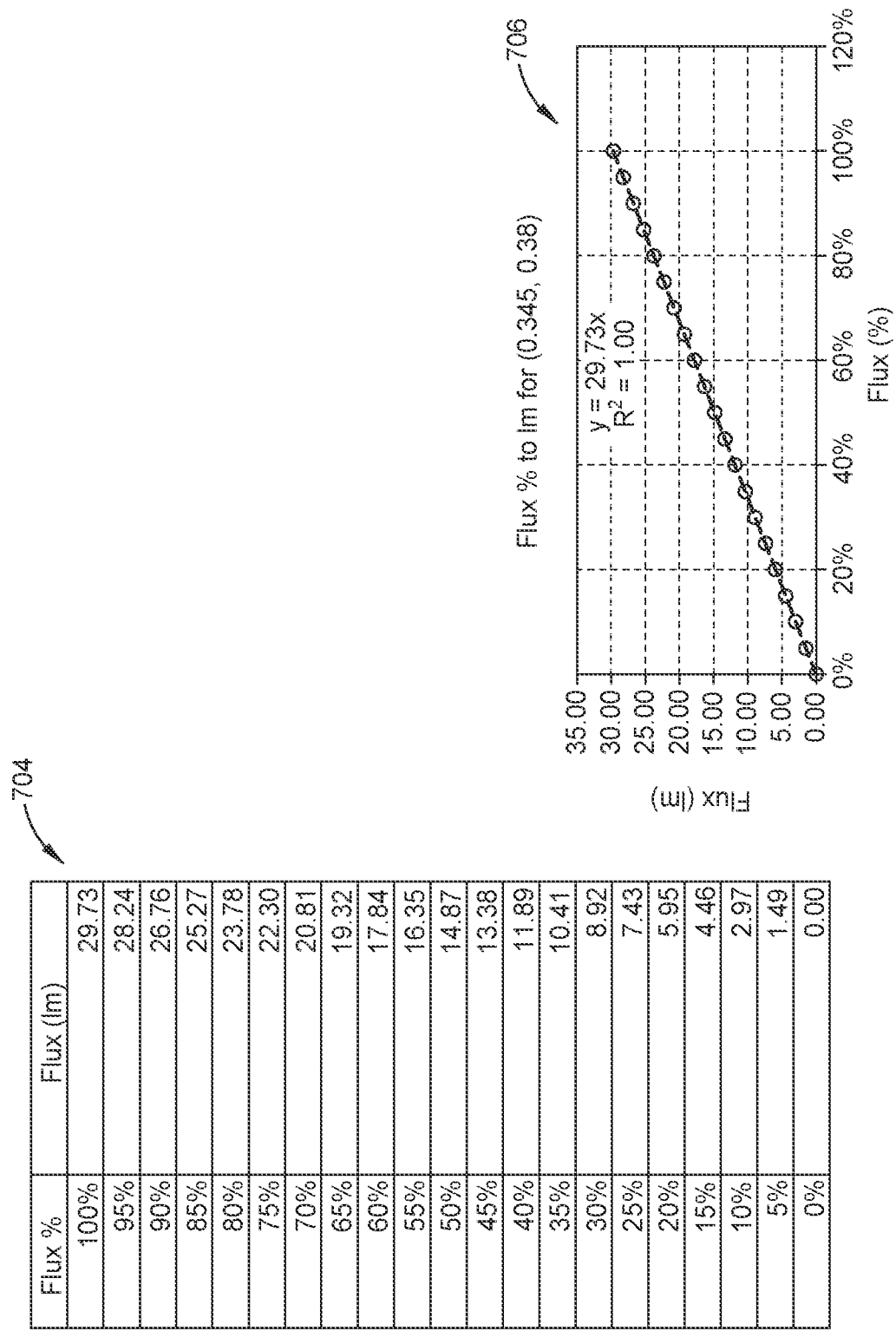
FIG. 7C illustrates an example experimental table and corresponding example graph as determined during the method of FIG. 6, in accordance with certain embodiments of the present disclosure.
Figure 7D:
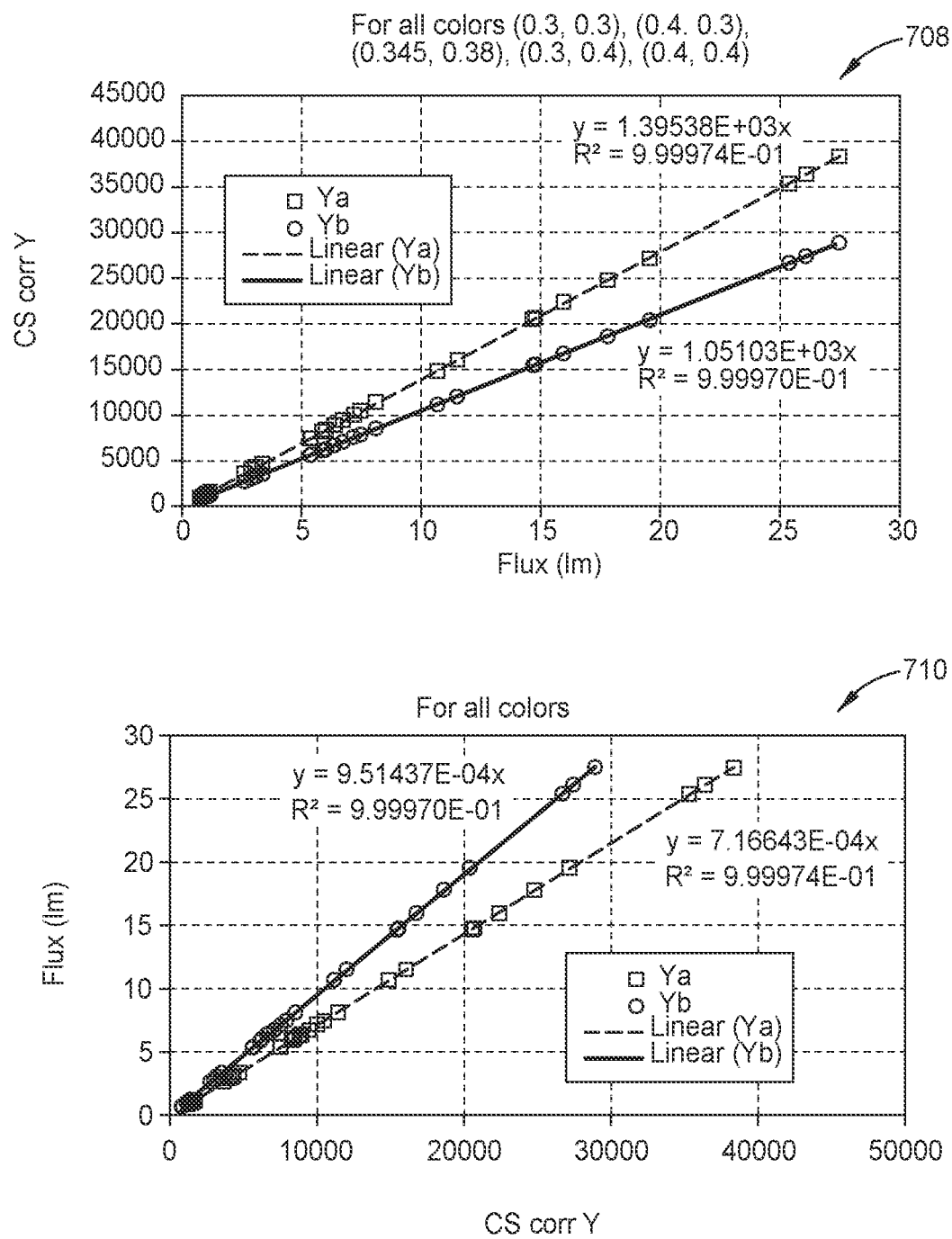
FIG. 7D illustrates example fitted polynomial curves as determined during the method of FIG. 6, in accordance with certain embodiments of the present disclosure.

For illustrative purposes, a representative table 704 and corresponding graph 706 are shown in FIG. 7C to illustrate the mapping of target outputs to output setting value steps at operation 606, as applied to the light engine 208 in the examples of FIGS. 7A and 7B. In the examples of FIG. 7C, the estimated maximum output flux is 29.73 lm. Accordingly, a desired output setting value of 5% corresponds to a target output flux of 1.49 lm, a desired output setting value of 10% corresponds to a target output flux of 2.97 lm, a desired output setting value of 15% corresponds to a target output flux of 4.46 lm, and so on. The mapped values form a linear relationship or function of target output flux and output setting values, as evidenced in graph 706.

Upon determining a target output flux value for each desired output setting of the light engine 208, the target output flux values are converted back to corresponding drive intensity values (e.g., PWM duty cycle times) that can be input into the light engine 208 to reproduce the target output flux values. Generally, this conversion is completed in a plurality of operations, beginning with operation 608.

At operation 608, a second polynomial fit (also referred to herein as a second function), is calculated to model a relationship between the measured output flux values of light engine 208, e.g., found in column Sp26 of initial table 700, and corrected color sensor Y values, e.g., corrected luminance readings found in column Sp9 as measured by a first color sensor, and column Sp14 as measured by a second color sensor. Though luminance readings from two separate sensors are presented in table 700, only one set of luminance readings from a single color sensor is sufficient for operation 608, as previously described. Thus, the two sets of readings are redundant, and either set of values from the first color sensor or the second color sensor may be utilized.

The color sensor Y values listed in either column Sp9 or Sp14 are color sensor readings that are proportional to a luminous flux of the light engine 208 when shined upon the color sensor. The light shining upon the color sensor is a very small portion of the total flux from the light engine 208 that is directed towards the sensor by an internal optical beamsplitter. Therefore, the flux of this small portion of light is highly correlated to the output flux of the light engine 208. Accordingly, the color sensor Y values provide a constant for all desired pre-set colors, and the relationship between the color sensor Y values and measured output flux of the light engine 208 can be utilized as a bridge for converting the output setting values (i.e., the percentages in representative table 704) into the desired drive intensity that will cause the light engine 208 to produce the target output flux values previously mapped to the output setting values. The relationship between measured output flux and color sensor Y values in the examples of FIGS. 7A-7C is illustrated in graphs 708 and 710 of FIG. 7D. In particular, graph 708 depicts measured output flux plotted along the X-axis and corrected color sensor Y values plotted along the Y-axis, while graph 710 illustrates the same data on inverted or reversed axes. As shown in both graphs, the measured flux and color sensor Y readings exhibit a linear relationship, and only a single polynomial fit or function is typically calculated to model the relationship.

At operation 610, using the modeled relationship of measured flux and color sensor Y values for the light engine 208, additional mappings are determined between target output flux values for each desired output setting value and the adjusted color sensor Y values. To illustrate the mappings at operation 610, a representative table 712 is illustrated in FIG. 7E. Representative table 712 includes the target output flux values for each desired output setting value as found in table 704, but also further includes columns, labelled "corr Ya" and "corr Yb," for adjusted color sensor Y values mapped to (e.g., calculated for) the previously determined output setting values and target output flux values. The adjusted color sensor Y values for each output setting value may be determined utilizing the following formula, where "a" is a coefficient of the fitting parameter as determined at operation 608:

Adj. Color Sensor $Y = (a) \times (\text{Flux(lm)})$.

Figure 7F:
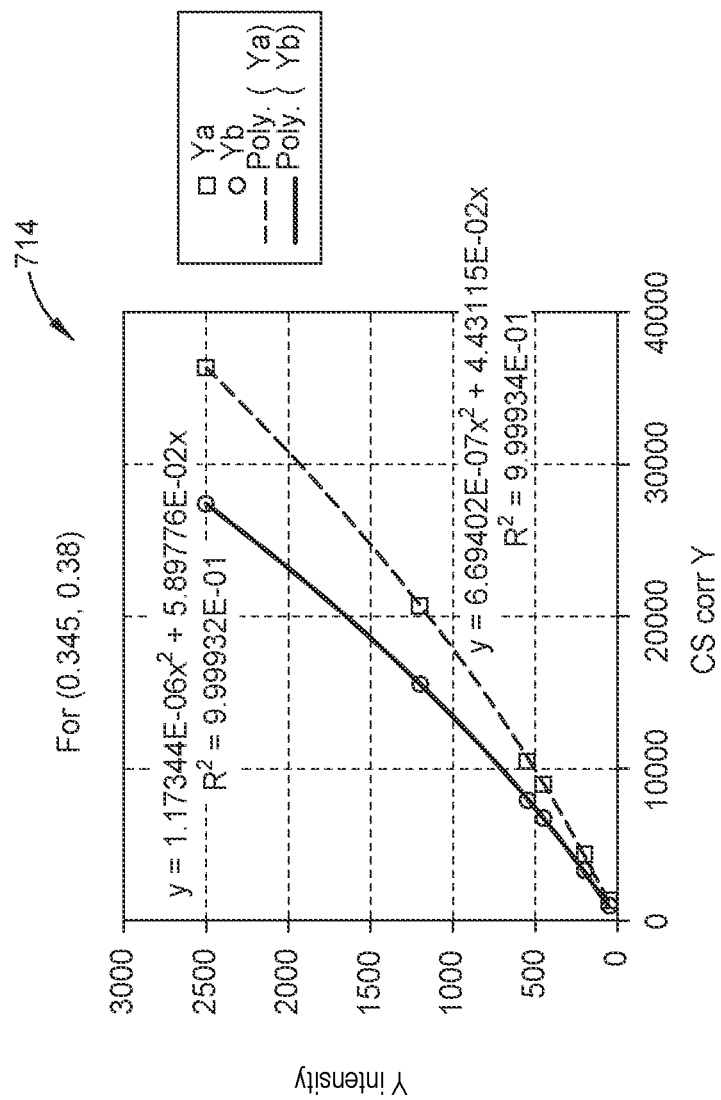
FIG. 7F illustrates example fitted polynomial curves as determined during the method of FIG. 6, in accordance with certain embodiments of the present disclosure.

At operation 612, the adjusted color sensor Y values, as determined for each target output flux value and desired output setting value of light engine 208, are mapped to the drive intensity values for the primary electrical input parameter found in column Sp4 of initial data table 700. Accordingly, a third polynomial fit, or third function, is calculated to model the direct relationship between the adjusted color sensor Y values, e.g., columns "corr Ya" and "con Yb" in representative table 712, and drive intensity, which generally produces two fitting parameters. An example graph 714 is depicted in FIG. 7F, which shows the adjusted color sensor Y values plotted along the X-axis, and drive intensity values plotted along the Y-axis. In representative graph 714, data from each of two color sensors is illustrated, though, as previously described, only data from a single color sensor may be used. The illustrated relationships in graph 714 are color-dependent and thus, must be calculated for each desired pre-set color of the light engine 208 during calibration.

At operation 614, the adjusted color sensor Y values, target output flux values, and output setting values (e.g., in dimensionless (percentage) units) are further mapped to the adjusted drive intensity values. Adjusted drive intensity may be determined utilizing the following formula, where "a" and "b" are coefficients of the fitting parameters determined at operation 612:

Adj. Drive $= (a) \times (\text{Adj. Color Sensor } Y)^2 + (b) \times (\text{Adj. Color Sensor } Y)$.

Once the adjusted drive intensity values are determined, a percentage (%) of each adjusted drive intensity value relative to the maximum drive intensity (in the examples of FIGS. 7A-7F, the maximum drive intensity value is 3200) is calculated, utilizing the following formula:

Adj. Drive % $= (\text{Adj. Drive})/(\text{Maximum Drive}) \times 100\%$.

A representative table 716, populated with adjusted drive intensities and drive intensity percentages of light engine 208 based on the examples of FIGS. 7A-7F, is illustrated in FIG. 7G. As shown, a maximum drive intensity percentage calculated at operation 614 is less than 100% (93.45% for the first color sensor, and 93.40% for the second color sensor). Therefore, at operation 616, the calculated adjusted drive intensities are scaled in order to create a full range of adjusted drive intensity values from 0-100% of the maximum drive intensity. Another representative table 718, which includes scaled adjusted drive intensity values, is illustrated in FIG. 7H. As shown, the previously un-scaled adjusted drive intensity values are scaled up to 100%, thus equaling 3200 and covering the full range of achievable drive intensities for the primary electrical input parameter (e.g., maximum supported PWM duty cycle to drive LEDs). Note that although the examples in FIG. 7A-7H are scaled up at operation 616, in certain embodiments, the adjusted drive intensities may be scaled down. Generally, the adjusted drive intensity values may be scaled utilizing the following formula:

Scaled Adj. Drive % $= (a) \times (\text{Adj. Drive \%})$, wherein "a" is a scaling factor determined by the following formula:

$$a=(\text{Maximum Drive})/(\text{Maximum Adj. Drive}).$$

Upon scaling, the scaled adjusted drive values are now mapped to the previously correlated adjusted and un-scaled drive intensities and drive intensity percentages, adjusted color sensor Y values (for one or more sensors), target output flux values, and output setting values (e.g., data found in representative table 712). A representative table 720 depicting the aforementioned scaled mappings is illustrated in FIG. 7I for reference.

Figure 7J:
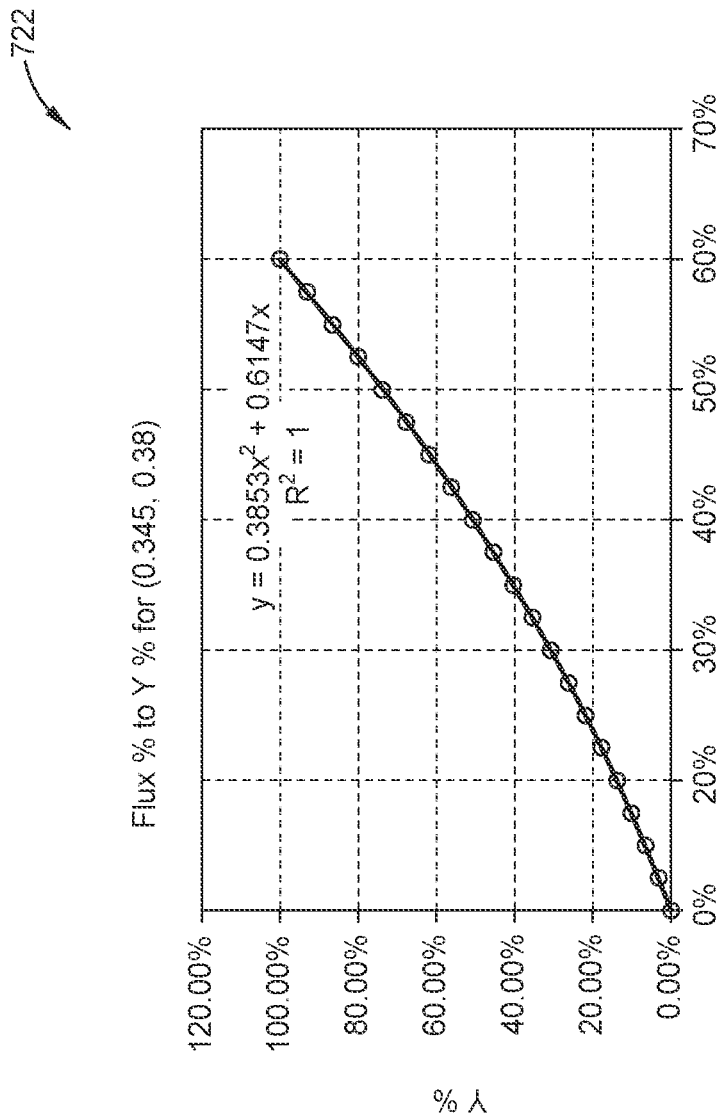
FIG. 7J illustrates an example fitted polynomial curve as determined during the method of FIG. 6, in accordance with certain embodiments of the present disclosure.

Using the scaled mappings (e.g., data found in representative table 720), a final relationship may be determined between the output setting values, in percentages, and the scaled and adjusted drive intensity percentages for a particular pre-set color. Thus, at operation 618, a fourth polynomial fit, or fourth function, is calculated to model the relationship between the output setting values and scaled and adjusted drive intensity percentages, which typically yields two fitting parameters. A representative graph 722 of this relationship is depicted in FIG. 7J, which shows the output setting values plotted along the X-axis, and scaled and adjusted drive intensity percentages plotted along the Y-axis. The two fitting parameters derived from the modeled relationship enables a customized conversion from a desired output setting value of the light engine 208, to an adjusted drive intensity for a primary electrical input parameter of the light engine 208, which causes the light engine 208 to produce an illumination light with a perceived brightness that matches desired output setting value. As a result, when a user, such as a surgeon, adjusts to a desired output setting of the light engine 208, e.g., while using a surgical system with an illuminator, the observed brightness of the light engine 208 will correspond to the output setting adjustment.

In summary, embodiments of the present disclosure generally relate to systems and methods for calibrating light-emitting diode (LED) light engines, and more specifically, to systems and methods for calibrating LED light engines to facilitate utilization of dimensionless output setting values reflecting an observed brightness of illumination. The methods and systems described herein address the deficiencies of certain existing LED illumination systems, wherein an adjustment in the desired output setting of a light engine results in a non-linear and non-intuitive adjustment in observed brightness. Accordingly, the methods and systems described herein may be utilized to calibrate a light engine so that an observed brightness of a produced illumination light linearly corresponds to a user-input increase or decrease in an output setting value.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

EXAMPLE EMBODIMENTS

Embodiment 1: A method of producing a calibrated illumination light with an illumination system having a light engine, comprising: receiving a user input corresponding to a dimensionless output setting value of the illumination system; mapping the dimensionless output setting value to a corresponding adjusted drive intensity of a light engine input using a mapping, wherein the mapping is derived by: obtaining a first set of data for the light engine, wherein the first set of data includes measured output flux data of the light engine and color sensor luminance readings, wherein the measured output flux data and the color sensor luminance readings correspond to drive intensity data of a light engine input parameter; determining a first relationship between the measured output flux data and the drive intensity data; determining a second relationship between the measured output flux data and the color sensor luminance readings; determining a third relationship between the drive intensity data and the color sensor luminance readings; and determining a fourth relationship between the dimensionless output setting value and the drive intensity data of the light engine input parameter, wherein the fourth relationship enables conversion of the dimensionless output setting value to a corresponding adjusted drive intensity of the light engine input parameter for driving the light engine to producing an illumination light with a desired output flux; and driving the light engine with the adjusted drive intensity to produce the illumination light with the desired output flux.

What is claimed is:
1. A method of producing calibrated illumination light with a light engine of an illumination system, comprising:
   obtaining a first set of data for the light engine, wherein the first set of data includes measured output flux data of the light engine and color sensor luminance readings, wherein the measured output flux data and the color sensor luminance readings correspond to drive intensity data of a light engine input parameter;
   determining a first mapping between the measured output flux data and the drive intensity data;
   determining a second mapping between the measured output flux data and the color sensor luminance readings;
   determining a third mapping between the drive intensity data and the color sensor luminance readings, based on the first mapping and the second mapping;

determining, based on the third mapping, a fourth mapping between a plurality of dimensionless output setting values of the illumination system and the drive intensity data;

receiving one of the plurality of dimensionless output setting values from a user input;

matching the one of the plurality of dimensionless output setting values to a corresponding drive intensity of the light engine input parameter using the fourth mapping; and producing, using the light engine, illumination light with a desired output flux.

2. The method of claim 1, wherein the first mapping corresponds to a polynomial fit between the measured output flux data and the drive intensity data.

3. The method of claim 1, wherein the second mapping corresponds to a polynomial fit between the measured output flux data and the color sensor luminance reading.

4. The method of claim 1, wherein the third mapping corresponds to a polynomial fit between the drive intensity data and the color sensor luminance readings.

5. The method of claim 1, wherein the fourth mapping corresponds to a polynomial fit between the plurality of dimensionless output setting values and the drive intensity data.

6. The method of claim 1, wherein the first mapping is used to estimate a maximum output flux of the light engine.

7. The method of claim 6, wherein the maximum output flux of the light engine is used to determine a full range of target output flux values, each target output flux value corresponding to one of the plurality of dimensionless output setting values.

8. The method of claim 7, wherein the second mapping is used to determine adjusted color sensor luminance readings, each of the adjusted color sensor luminance readings corresponding to one of the full range of target output flux values.

9. The method of claim 8, wherein the third mapping is used to determine an adjusted drive intensity corresponding to each of the adjusted color sensor luminance readings.

10. The method of claim 9, wherein the adjusted drive intensities are scaled to correspond to the full range of target output flux values.

11. The method of claim 1, wherein determining the second mapping between the measured output flux data and the color sensor luminance readings is independent of a color of light produced by the light engine.

12. The method of claim 11, wherein determining the first, third, and fourth mappings is dependent upon a color of light produced by the light engine.

* * * * *